US008436182B2

(12) United States Patent
Zegrocka-Stendel et al.

(10) Patent No.: US 8,436,182 B2
(45) Date of Patent: May 7, 2013

(54) PROCESS FOR PREPARATION OF SOLIFENACIN AND/OR THE PHARMACEUTICALLY ACCEPTABLE SALTS THEREOF OF HIGH PHARMACEUTICAL PURITY

(75) Inventors: Oliwia Zegrocka-Stendel, Lomianki (PL); Joanna Zagrodzka, Warsaw (PL); Marta Laszcz, Warsaw (PL)

(73) Assignee: Zaklady Farmaceutyczne Polpharma SA, Starogard Gdanski (PL)

( * ) Notice: Subject to any disclaimer, the term of this patent is extended or adjusted under 35 U.S.C. 154(b) by 187 days.

(21) Appl. No.: 12/993,988

(22) PCT Filed: May 22, 2009

(86) PCT No.: PCT/PL2009/000054
§ 371 (c)(1),
(2), (4) Date: Dec. 1, 2010

(87) PCT Pub. No.: WO2009/142522
PCT Pub. Date: Nov. 26, 2009

(65) Prior Publication Data
US 2011/0065922 A1     Mar. 17, 2011

(30) Foreign Application Priority Data

May 23, 2008  (PL) .......................................... 385265

(51) Int. Cl.
*C07D 217/02*  (2006.01)
(52) U.S. Cl.
USPC ........................................................ 546/144
(58) Field of Classification Search ........................ None
See application file for complete search history.

(56) References Cited

U.S. PATENT DOCUMENTS

| 4,001,244 A | 1/1977 | Yonan |
| 2011/0077405 A1 | 3/2011 | Zegrocka-Stendel et al. |

FOREIGN PATENT DOCUMENTS

| EP | 0801067 A1 | 10/1997 |
| EP | 1757604 A1 | 2/2007 |
| WO | 2005105795 A1 | 11/2005 |
| WO | 2007147374 A2 | 12/2007 |
| WO | 2008/011462 | 1/2008 |
| WO | 2008/019055 | 2/2008 |
| WO | 2008/019057 | 2/2008 |

OTHER PUBLICATIONS

Naito Ryo et al., "Synthesis and Antimuscarinic Properties of Quinuclidin-3-yl1,2,3,4-Tetrahydroisoquinoline-2-carboxylate Derivatives as Novel Muscarinic Receptor Antagonists", Journal of Medicinal Chemistry. American Chemical Society, Washington, U.S. vol. 48, No. 21, pp. 6597-6606, Oct. 20, 2005.
Leithe et al., "Uber die naturliche drehung des polarisierten lichtes durch optisch aktive basen iv. die drehung einiger synthetischer isochinolinderivate" Monatshefte fur chemie, springer verlag, wien, AT vol. 53,54, 1929 pp. 956-962 (English Abstract attached) Natural rotation of polarized light by optically active bases. IV. Rotation of several synthetic isoquinoline derivatives.
International Search Report from International Application No. PCT/PL2009/000053 dated Aug. 26, 2009. (Copending application—U.S. Appl. No. 12/993,874, filed Nov. 22, 2010).
International Search Report from International Application No. PCT/PL2009/000054 dated Aug. 13, 2009.
International Preliminary Report on Patentability of PCT/PL2009/000053 dated Dec. 2, 2010.
Written Opinion of the International Searching Authority of PCT/PL2009/000053.

*Primary Examiner* — Zinna Northington Davis
(74) *Attorney, Agent, or Firm* — Roberts Mlotkowski Safran & Cole, P.C.

(57) ABSTRACT

A process for the preparation of solifenacin and/or the pharmaceutically acceptable salts thereof of high pharmaceutical purity is characterized in that 3-(R)-quinuclidinoloxy anion generated in situ from 3-(R)-quinuclidinol in a presence of strong base in polar organic solvent is subject to acylation with (S)-1-phenyl-1,2,3,4-tetrahydroisoquinolinecarbonyl chloride of chemical purity at least 98%, while maintaining constant anion excess in a reaction mixture, and after reaction completion solifenacin base is optionally transformed into solifenacin salt according to standard procedures. (S)-1-Phenyl-1,2,3,4-tetrahydroisoquinolinecarbonyl chloride of chemical purity at least 98% is obtained in a reaction of (S)-1-phenyl-1,2,3,4-tetrahydroisoquinoline and molar excess of phosgene in a presence of tertiary aromatic amine in aromatic hydrocarbon, and isolated in a crystalline form.

10 Claims, 2 Drawing Sheets

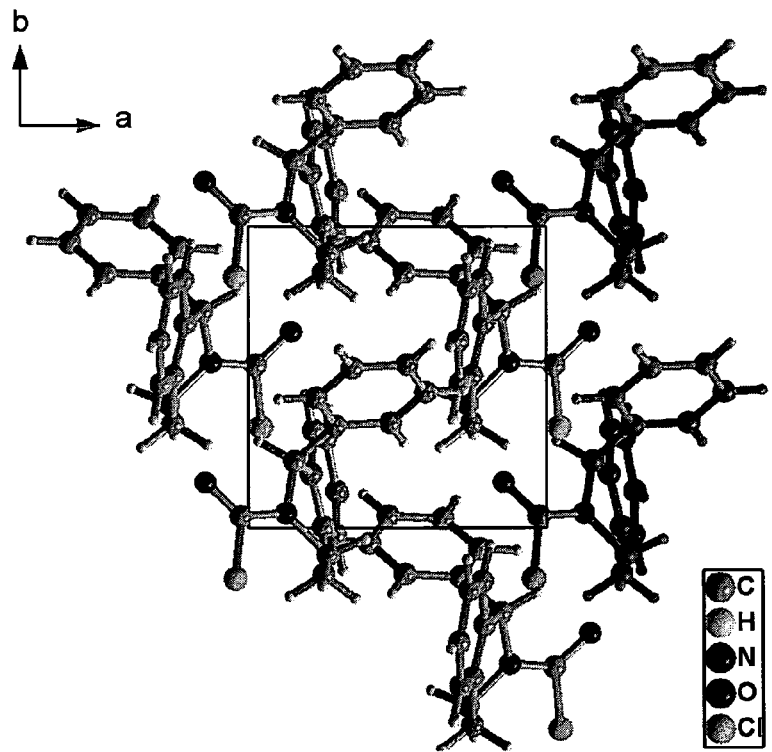
Fig. 1. Projection of 1-(S)-phenyl-1,2,3,4-tetrahydroisochinolinecarbonyl chloride molecule along c axis.
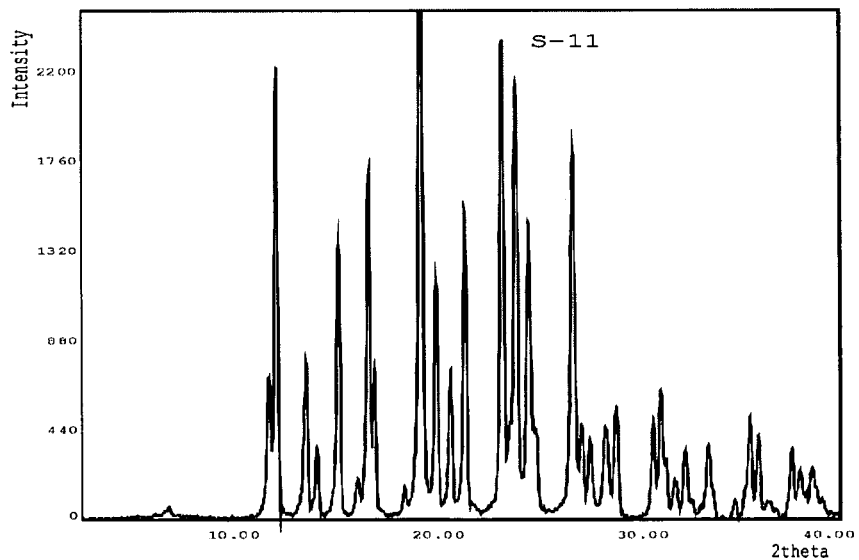
Fig. 2. X-ray powder diffractogram of 1-(S)-phenyl-1,2,3,4-tetrahydroisochinolinecarbonyl chloride

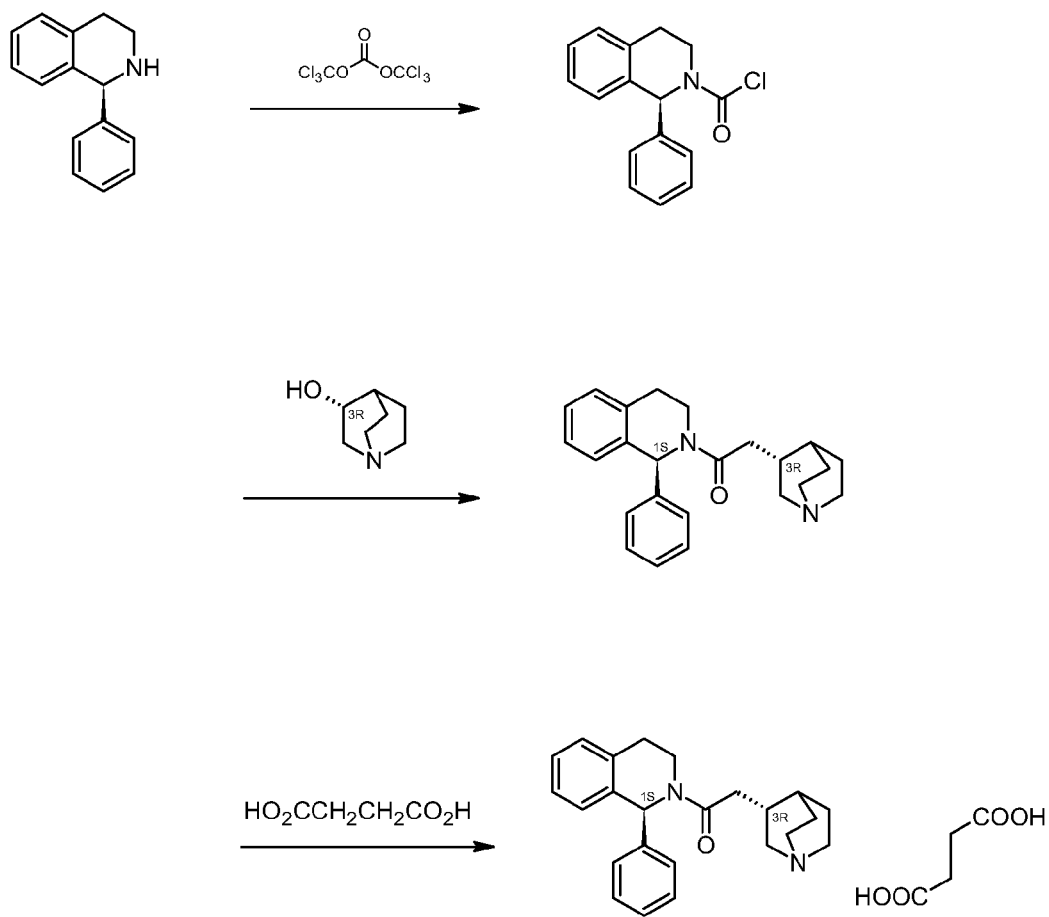
Fig. 3 A process scheme for the preparation of solifenacin succinate

PROCESS FOR PREPARATION OF SOLIFENACIN AND/OR THE PHARMACEUTICALLY ACCEPTABLE SALTS THEREOF OF HIGH PHARMACEUTICAL PURITY

CROSS-REFERENCE TO RELATED APPLICATIONS

The present Application is a US national phase of PCT/PL2009/000054 filed on May 22, 2009 ("PCT Application"), which claims priority from Polish Application No. 385265 filed on May 23, 2008, both of which are hereby incorporated by reference in their entirety into the present Application.

FIELD OF THE INVENTION

The inventions relates to the process for preparation of solifenacin and/or the pharmaceutically acceptable salts thereof of high pharmaceutical purity.

Solifenacin, (R)-3-quinuclidinol (1S)-1-phenyl-1,2,3,4-tetrahydroisoquinolin-2-carboxylate (IUPAC name: 1-azabicyclo[2.2.2]oct-8-yl (1S)-1-phenyl-3,4-dihydroisoquinoline-2-carboxylate), is a competitive selective M3 muscarinic receptor antagonist. Solifenacin succinate is the active substance of Vesicare®, licensed for the treatment of overactive bladder symptoms of urge urinary incontinence, urgency and urinary frequency.

BACKGROUND OF THE INVENTION

In general, there are two synthetic approaches concerning preparation of solifenacin, either as a racemic mixture or biologically active pure isomer (1S, 3'R). One of them is based on the reaction of quinuclidinol and 1-phenyl-1,2,3,4-tetrahydroisoquinoline carbamoyl derivative with good leaving group. Another approach regards the condensation of 1-phenyl-1,2,3,4-tetrahydroisoquinoline and active quinuclidinol derivative, such as chloroformate or carbonate for instance. In EP 0801067 B1 and WO 2005/105795 chloride, lower alkoxides and phenoxide groups as well as 1H-imidazol-1-yl, 2,5-dioxopyrrolidin-1-yloxyl and 3-methyl-1H-imidazol-3-ium-1-yl were mentioned as good leaving groups in this process.

In European patent EP 0801067 B1, transesteryfication of carbamoyl ethyl ester derivative of 1-phenyl-1,2,3,4-tetrahydroisoquinoline racemic mixture proceeded in toluene suspension in the presence of sodium hydride; obtained diastereoisomeric mixture of products was resolved due to chiral high-pressure liquid chromatography technique.

In *J. Med Chem.*, 2005, 48 (21), 6597-6606, instead of the racemic mixture, ethyl (S)-1-phenyl-1,2,3,4-tetrahydroisoquinoline-2-carboxylate as pure enantiomer was used. This optically active semiproduct was obtained in the prior step, in the reaction of (S)-1-phenyl-1,2,3,4-tetrahydroisoquinoline and ethyl chloroformate in the presence of potassium carbonate.

The above mentioned methods require use of sodium hydride as well as expensive, optically active (R)-quinuclidinol in big excess. In addition, this reaction proceeds in moderate yield about 50%, that makes the process not suitable in an industrial scale manufacturing process.

In EP 0801067 B1, the possibility of solifenacin preparation in the condensation reaction of (S)-1-phenyl-1,2,3,4-tetrahydroisoquinoline-2-carbamoyl chloride and (R)-3-quinuclidinol was also mentioned, however none preparative example of this process was given.

Synthetic route of solifenacin disclosed in WO 2005/105795 comprises the reaction of (S)-1-phenyl-1,2,3,4-tetrahydroisoquinolinecarbonyl chloride and (R)-quinuclidinol in the presence of base. In the example, (S)-1-phenyl-1,2,3,4-tetrahydroisoquinoline is treated with phosgene in toluene in the presence of triethylamine. After addition of methanol and water to the reaction mixture, followed by evaporation of organic solvents, the reaction product is being isolated as an oil. The obtained intermediate in toluene solution is then added to the mixture of (R)-3-quinuclidinol and sodium hydride in toluene at reflux. The reaction is carried out under the same conditions overnight. Authors of this publication claimed that, 'solifenacin formation had been confirmed', but neither yield nor purity of thus obtained product was revealed. Following thereinbefore procedure, the present Inventors obtained solifenacin of purity less than 43% according to HPLC analysis.

The route of synthesis comprising the reaction of 1-phenyl-1,2,3,4-tetrahydroisoquinoline and 3-quinuclidinol in dimethylformamide, described in EP 0801067, was reproduced in WO 2007/147374. The formation of substantial amount of symmetrically disubstituted urea derivative was observed which significantly reduced the yield of the main product. This by-product formation was ascribed to the acylation at 3-quinuclidinol nitrogen atom giving a quaternary ammonium salt, the salt hydrolysis with further decarboxylation of the formed acid, followed by the reaction of the thus obtained 1-phenyl-1,2,3,4-tetrahydroisoquinoline with the residue of the acylation agent.

Except for detailed considerations of the reaction mechanism, we established, the uretane by-product with two chiral carbon atoms is obtained under very similar conditions also in case the optically active reagents are used. On account of low solubility in organic solvents, this disubstituted uretane derivative is difficult to get rid off the final product, using standard purification methods, for example, crystallization. Therefore, to obtain solifenacin of pharmaceutical purity, the formation of urethane by-product should be significantly diminished prior to converting solifenacin into its pharmaceutically acceptable salt.

The pharmaceutical substances authorized for human use must meet the requirements established by International Conference on Harmonization of Technical Requirements for Registration of Pharmaceuticals for Human Use (ICH). These standards impose the necessity to develop new, more effective methods of solifenacin and the salts thereof synthesis, in comparison to the processes known in the prior art. Whenever hereafter a reference is made to 'solifenacin of pharmaceutical purity', is to be understood solifenacin or its salts with pharmaceutically acceptable acids, including less than 0,1% of single impurities or less than 0,4% of unidentified impurities in total.

Attempts made to obtain solifenacin of pharmaceutical purity in the reaction of (S)-1-phenyl-1,2,3,4-tetrahydroisoquinolinecarbonyl chloride and (R)-quinuclidinol proved, that purity of the final product strongly depends on the purity of (S)-1-phenyl-1,2,3,4-tetrahydroisoquinolinecarbonyl chloride used in this reaction. It is generally known that (S)-1-phenyl-1,2,3,4-tetrahydroisoquinolinecarbonyl chloride may be synthesized from chiral 1-(S)-phenyl-1,2,3,4-tetrahydroisoquinoline upon treatment with carbonylating reagent, such as gaseous carbon oxychloride (phosgene), liquid trichloromethyl chloroformate (diphosgene), solid bis-(trichloromethyl) carbonate (triphosgene), urea and other. Some impurities accompanying (S)-1-phenyl-1,2,3,4-tetrahydroisoquinolinecarbonyl chloride, especially the residues of unreacted 1-(S)-phenyl-1,2,3,4-tetrahydroisoquinoline impede purification of solifenacin. On account of similar polarity of 1-(S)-phenyl-1,2,3,4-tetrahydroisoquinoline and solifenacin base, the succinate salt of the former co-crystallizes with the final solifenacin succinate. As it was said before, 1-(S)-phenyl-1,2,3,4-tetrahydroisoquinoline reacts with solifenacin obtained in the next step, thereupon undesired uretane by-product is formed.

SUMMARY OF THE INVENTION

Unexpectedly, efficacious process for synthesis of solifenacin and the salts thereof free of undesirable by-products, was developed by the present Inventors. This process, useful to be implemented in a industrial scale production, is based on providing (S)-1-phenyl-1,2,3,4-tetrahydroisoquinolinecarbonyl chloride of purity not less than 98% and its use in the acylation reaction of 3-(R)-quinuclidinol.

The present invention provides the process for the preparation of solifenacin and/or the pharmaceutically acceptable salts thereof of high pharmaceutical purity, characterized in that 3-(R)-quinuclidinoloxy anion generated in situ from 3-(R)-quinuclidinol in a presence of strong base in polar organic solvent is subject to acylation with (S)-1-phenyl-1,2,3,4-tetrahydroisoquinolinecarbonyl chloride of chemical purity at least 98%, while maintaining constant anion excess in a reaction mixture, and after reaction completion solifenacin base is optionally transformed into solifenacin salt according to standard procedures.

The other aspect of the invention is the process for the preparation of (S)-1-phenyl-1,2,3,4-tetrahydroisoquinolinecarbonyl chloride of chemical purity at least 98% from chiral (S)-1-phenyl-1,2,3,4-tetrahydroisoquinoline.

Another aspect of the invention is (S)-1-phenyl-1,2,3,4-tetrahydroisoquinolinecarbonyl chloride obtained as crystalline solid, isolated during the preparation process of solifenacin.

BRIEF DESCRIPTION OF FIGURES

FIG. 1 represents the projection of crystalline (S)-1-phenyl-1,2,3,4-tetrahydroisoquinolinecarbonyl chloride along c axis.

FIG. 2 represents X-ray powder diffraction pattern of (S)-1-phenyl-1,2,3,4-tetrahydroisoquinolinecarbonyl chloride.

FIG. 3 represents a process scheme for the preparation of solifenacin succinate.

DETAILED DESCRIPTION OF THE INVENTION

As shown in FIG. 3, (S)-1-Phenyl-1,2,3,4-tetrahydroisoquinolinecarbonyl chloride of chemical purity suitable to be employed in the solifenacin synthesis according to present invention, is preferably obtained in the reaction of (S)-1-phenyl-1,2,3,4-tetrahydroisoquinoline and molar excess of triphosgene, in a presence of tertiary aromatic amine, as a hydrochloride scavenger. Use of aromatic amine prevents from formation of additional impurities, which may be formed due to demethylation of aliphatic amines in a presence of phosgene.

Preferably, the amount of triphosgene used according to the invention represents 5-15% molar excess, in respect to stoichiometric quantity of phosgene, which is the proper carbonylating agent.

Suitable aromatic amine is pyridine.

The reaction is carried out at 70-90° C. in an inert solvent, preferably aromatic hydrocarbon, such as for example toluene. Reaction runs in almost quantitative yield. Precipitated pyridine hydrochloride is removed form the post-reaction mixture and the mixture is evaporated to oily residue. (S)-1-Phenyl-1,2,3,4-tetrahydroisoquinolinecarbonyl chloride obtained under these conditions is characterized by high chemical purity. When dissolved in non-polar aprotic solvent, preferably heptan, optionally with addition of some amount of polar solvent (for example tetrahydrofurane), preventing from crystallization, it may be directly used in the synthesis of pharmaceutically pure solifenacin.

It was observed, that chemical purity of (S)-1-phenyl-1,2,3,4-tetrahydroisoquinolinecarbonyl chloride may be improved using in the reaction suitable solvent, in which the impurities are not soluble and the intermediate is isolated in crystalline form. (S)-1-Phenyl-1,2,3,4-tetrahydroisoquinolinecarbonyl chloride of chemical purity 98-99% is obtained without the need for re-crystallization, when non-polar aprotic solvent, most preferably heptan, is used.

In the preferred embodiment of the invention, (S)-1-phenyl-1,2,3,4-tetrahydroisoquinolinecarbonyl chloride obtained in oily form is dissolved at reflux in non-polar aprotic solvent, most preferably in heptan. The solution is filtered and left at 5-10° C. for crystallization, the crystalline solid is isolated either by filtration or decantation.

Thus obtained crystalline (S)-1-phenyl-1,2,3,4-tetrahydroisoquinolinecarbonyl chloride is characterized by purity of 98-99% (analyzed by HPLC).

Crystal structure of (S)-1-phenyl-1,2,3,4-tetrahydroisoquinolinecarbonyl chloride, which was not published in a literature up till now, has been solved by single crystal X-ray analysis. Density calculated as well as parameters measured are collected in Table 1.

TABLE 1

| Crystal data and structure refinement | |
|---|---|
| Molecular formula | $C_{16}H_{14}ClNO$ |
| Molecular weight | 271.73 |
| Temperature of measurement | 100 K |
| Wavelength | 0.71073 Å |
| Crystal system | Monoclinic |
| Space group | P2(1) |
| Unit cell dimensions | [Å]: a = 7.5153(2), b = 7.3857(3), c = 12.4080(4) [°]: $\alpha$ = 90, $\beta$ = 104, 172(3), $\gamma$ = 90 |
| Unit cell volume | 667.75(4) Å$^3$ |
| Number of molecules in unit cell, Z | 2 |
| Density (calculated) | 1.351 g/cm$^3$ |
| Absorption coefficient | 0.276 mm$^{-1}$ |
| F (000) | 284 |
| Crystal dimensions | 0.72 × 0.40 × 0.09 mm |
| Theta range for data collection, $\theta$ | 2.80-28.67° |
| Limiting indices hkl | −10 <= h <= 10, −9 <= k <= 9, −16 <= l <= 16 |
| Reflections collected/unique | 12305/3200 [R(int) = 0.0157] |
| Refinement metod | Full-matrix least-squares on F$^2$ |
| Data/restraints/parameters | 3200/1/172 |
| Goodness-of-fit (GOOF) | 1.077 |
| R [I > 2sigma(I)] | R1 = 0.0239, wR2 = 0.0629 |
| R (all data) | R1 = 0.0266, wR2 = 0.0637 |
| Largest diff. peak and hole | 0.219 and −0.181 eÅ$^{-3}$ |

The packing of molecules in crystal lattice is depicted in FIG. 1

The crystalline (S)-1-phenyl-1,2,3,4-tetrahydroisoquinolinecarbonyl chloride isolated in the process of the invention is characterized by an X-ray powder diffraction pattern (XRPD) substantially as presented in FIG. 2.

At the X-ray diffraction pattern the characteristic peaks are observed presented as the relation of interplanar distances d (Å), diffraction angles 2θ (°), and relative intensities, in attitude to the most intensive diffraction peak, $I/I_o$ (%), as it is depicted in Table 2:

TABLE 2

X-ray powder diffraction of (S)-1-phenyl-1,2,3,4-tetrahydroisoquinolinecarbonyl chloride

| d [Å] | 2θ [°] | $I/I_o$ [%] |
|---|---|---|
| 12.203 | 7.24 | 2 |
| 7.317 | 12.09 | 20 |
| 7.090 | 12.47 | 65 |
| 6.362 | 13.91 | 23 |
| 6.128 | 14.44 | 10 |
| 5.219 | 16.98 | 49 |
| 4.536 | 19.55 | 100 |
| 4.374 | 20.29 | 34 |
| 4.228 | 20.99 | 21 |
| 4.090 | 21.71 | 44 |
| 3.776 | 23.54 | 69 |
| 3.672 | 24.21 | 62 |
| 3.586 | 24.81 | 43 |
| 3.301 | 26.99 | 53 |
| 3.066 | 29.10 | 16 |

In the crucial step of the preparation of solifenacin according to the invention, (R)-3-quinuclidinoloxy anion, generated in situ, is reacted with (S)-1-phenyl-1,2,3,4-tetrahydroisoquinolinecarbonyl chloride. The latter may be added as a solution of crystalline form dissolved in polar aprotic solvent or crude oil dissolved in a mixture of aprotic polar and non-polar solvents.

Methods of organic anions generation are known to those skilled in the art and they comprise the treatment with strong bases, such as for example, alkali metals hydrides, especially sodium hydride; alkali metals alkoxides, for example potassium tert-butoxide; alkali metals hydroxides and carbonates, like for example sodium hydroxide or sodium carbonate. The reaction may be carried out either in one-phase or two-phase systems.

Reaction in two-phase system is performed using sodium hydroxide aqueous solution in polar aprotic solvent, such as tetrahydrofurane, dioxane, dimethylsulfoxide, dimethylformamide, dimethylacetamide, N-methylpyrrolidon, in a presence of phase transfer catalyst, especially quaternany ammonium salts, such as benzyl triethylammonium chloride, tetrabutylammonium bromide or tetrabutylammonium hydrosulfate.

In the preferred embodiment of the invention, (R)-3-quinuclidinoloxy anion is generated with the use of sodium hydroxide in polar aprotic solvent, such as tetrahydrofurane, dioxane, dimethylsulfoxide, dimethylformamide, dimethylacetamide, N-methylpyrrolidon, or their mixture.

In this embodiment, acylation reaction is carried out in one-phase system, in polar aprotic solvent, optionally with addition of non-polar solvent, such as pentan, heptan, hexane, cyclohexane, methylcyclohexane, which is used for dissolving (S)-1-phenyl-1,2,3,4-tetrahydroisoquinolinecarbonyl chloride.

Preferably, the acylation reaction is performed in tetrahydrofurane, optionally in a mixture with heptan.

The best mode of carrying out the invention is as follows. The solution of (S)-1-phenyl-1,2,3,4-tetrahydroisoquinolinecarbonyl chloride is slowly added to the suspension of generated in situ (R)-3-quinuclidinoloxy anion. Dropwise addition proceeds at room temperature to reflux of the reaction mixture, thereafter the solution is heated under reflux until the substrates are entirely consumed, while the reaction progress is being monitored by thin layer chromatography (TLC).

The present invention provides process (depicted at Fig.3) for the preparation of solifenacin of chemical purity suitable for its direct using to solifenacin pharmaceutically acceptable acid salts formation, especially solifenacin succinate, without additional purification.

Solifenacin succinate is obtained following standard procedures, reacting equimolar amount of solifenacin base and succinic acid in any organic solvent or in a mixture of solvents, in which solifenacin salt is formed. Suitable solvents include aliphatic alcohols, such as ethanol, butan-1-ol, 2-methyl butyl alcohol, isopropanol; ketones such as acetone, methyl isobutyl ketone; esters such as ethyl acetate, n-butyl acetate, ethyl propionate; aromatic hydrocarbons such as toluene; polar aliphatic hydrocarbons such as heptan. Crystalline product may be subject to additional crystallization from the same solvent the salt was formed, preferably from isopropanol.

Regardless of the solvent used, crystalline product characterized by the same X-ray powder diffractogram pattern is obtained. This fact proves, that solifenacin succinate crystallizes as one crystalline form.

Preferred embodiment of the invention comprises the process for the preparation of solifenacin, in which (S)-1-phenyl-1,2,3,4-tetrahydroisoquinoline is reacted with triphosgene in a presence of tertiary aromatic amine, preferably pyridine, in aromatic hydrocarbon, thereafter post-reaction mixture is evaporated and treated with non-polar aprotic solvent at reflux, left at 5-15° C. for crystallization, (S)-1-phenyl-1,2,3,4-tetrahydroisoquinolinecarbonyl chloride isolated as crystalline solid of 98% purity, preferably more than 99%, is dissolved in polar aprotic solvent and added to a suspension of generated in situ (R)-3-quinuclidinoloxide anion in the same solvent.

The present invention provides simple and efficient process for the preparation of solifencin and/or its pharmaceutically acceptable salts, especially solifenacin succinate characterized by high pharmaceutical purity.

The invention is illustrated by the following examples, which should not be construed as any limitation of its scope.

EXAMPLES

Methods of Measurements

Melting point was measured by differential scanning calorimetry with Mettler Toledo DSC 822 apparatus, using aluminum melting-pot, with heating speed 10° C./min. Melting point value is denominated as 'onset', which is determined as the cross-section of basic line and curve tangents.

Single crystal measurements were performed with single crystal diffractometer type κ-axis KM4CCD, for MoKα radiation.

X-Ray powder diffraction data were obtained using Rigaku X-ray powder diffractometer type MiniFlex equipped with CuKα detector, λ=1.54056, using the following measurement parameter:

scanning range 2θ from 3° to 40°
scanning rate Δω 0,5°/mon.
scanning step 0,03°
detector—scintillating counter Data obtained were worked up and analyzed using DHN_PDS program.

Example 1

A. (S)-1-Phenyl-1,2,3,4-tetrahydroisoquinolinecarbonyl chloride

In a three-neck flask the solution of triphosgene (10.87 g, 36.63 mmol) in toluene (60 mL) is prepared at room temperature (23° C.), then the reactor is placed in an ice-water cooling bath. In a separate flask (S)-1-phenyl-1,2,3,4-tetrahydroisoquinoline (20.0 g, 95.55 mmol, purity 99% (HPLC)) and pyridine (3.26 mL, 40.30 mmol) are placed in toluene (80 mL), while heating at 50-70° C. until the whole amount of solid is dissolved. After cooling down to room temperature, the clear toluene solution is transferred into a dropping funnel. The solution is added dropwise within ca. 10 min. to triphosgene in toluene solution. When the addition is complete, the cooling bath is removed and the reactor is submerged in an oil bath. Reaction mixture is heated at 70-80° C., in a mean time thick yellow solid slowly dissolves. Since reaction temperature reaches 50° C., heating and stirring is continued for 45 min., until disappearance of (S)-1-phenyl-1,2,3,4-tetrahydroisoquinoline signal (TLC control in $CH_2Cl_2$—MeOH 95:5, v/v against substrate sample) is observed. After completion of the reaction the mixture is cooled down to room temperature (20-24° C.), filtered through celit to remove precipitated pyridinium hydrochloride. Celit layer is washed with toluene (20 mL). Toluene (145 mL) is removed under reduced pressure (0.1-0.15 mmHg) from the post-reaction mixture, while heating the condensing flask in a water bath at 60-65° C. The oily residue is dissolved in heptan (200 mL) at reflux and the hot solution is filtered through celit (20 g), washed with heptan before filtration. The celit layer is washed with hot heptan (2×50 mL) after filtration. The excess of solvent (170 mL) is removed under reduced pressure; the condensed solution to ca. ½ volume is left at 5° C. for 12 h. Crystalline, colorless solid is filtered off and washed with heptan (2×15 mL). (S)-1-Phenyl-1,2,3,4-tetrahydroisoquinolinecarbonyl chloride is obtained in 23.3 g, 90% yield; purity (HPLC) 98.4%; $T_{(onset)}$=62.7° C.

B. Sollifenacin (R)-3-Quinuclidinol (11.0 g, 96.50 mmol) and 60% NaH (3.80 g, 95.10 mmol) are suspended in dry THF (70 mL), the resulting mixture is refluxed for 45 min. To obtained thick white suspension, (S)-1-phenyl-1,2,3,4-tetrahydroisoquinolinecarbonyl chloride (23.30 g, 86.0 mmol) in THF (50 mL) is added dropwise within 1 h at reflux. When addition is complete, stirring and heating is continued for 30 min. Reaction progress and total consumption of (S)-1-phenyl-1,2,3,4-tetrahydroisoquinolinecarbonyl chloride is monitored by TLC. The signal of forming product is observed in $CH_2Cl_2$—MeOH (9:1, v/v). After completion of the reaction, heating is stopped and the reaction mixture is cooled down to room temperature (20-24° C.). The solution is poured into water (100 mL). Layers are separated, water phase is extracted with toluene (3×50 mL), combined organic phases are washed with water (1×60 mL), dried ($Na_2SO_4$), filtered and condensed under reduced pressure to dryness. Creamy thick oil is obtained, which is subsequently used in the next step. Purity (HPLC) 97.19%.

Example 2

A. (S)-1-Phenyl-1,2,3,4-tetrahydroisoquinolinecarbonyl chloride

In a three-neck flask the solution of triphosgene (10.87 g, 36.63 mmol) in toluene (60 mL) is prepared at room temperature (23° C.), then the reactor is placed in an ice-water cooling bath. In a separate flask (S)-1-phenyl-1,2,3,4-tetrahydroisoquinoline (20.0 g, 95.55 mmol, purity 99% (HPLC)) and pyridine (3.26 mL, 40.30 mmol) are placed in toluene (80 mL), while heating at 50-70° C. until the whole amount of solid is dissolved. After cooling down to room temperature, the clear toluene solution is transferred into a dropping funnel. The solution is added dropwise within ca. 10 min. to triphosgene solution in toluene. When the addition is complete, the cooling bath is removed and the reactor is submerged in an oil bath. Reaction mixture is heated at 70-80° C., in a mean time thick yellow solid slowly dissolves. Since reaction temperature reaches 50° C., heating and stirring is continued for 45 min., until disappearance of (S)-1-phenyl-1,2,3,4-tetrahydroisoquinoline signal (TLC control in $CH_2Cl_2$—MeOH 95:5, v/v against substrate sample) is observed. After completion of the reaction the mixture is cooled down to room temperature (20-24° C.), filtered through celit to remove precipitated pyridinium hydrochloride. Celit layer is washed with toluene (20 mL). Toluene (145 mL) is removed under reduced pressure (0.1-0.15 mmHg) from the post-reaction mixture, while heating the condensing flask in a water bath at 60-65° C. The oily residue is dissolved in heptan (200 mL) at reflux and the hot solution is filtered through celit (20 g), washed with heptan before filtration. After filtration celit layer is washed with hot heptan (2×50 mL). Excess of solvent (170 mL) is removed under reduced pressure; the condensed solution to ca. ½ volume is diluted with THF (20 mL) to prevent crystallization of the intermediate. The solution is subsequently used in the nest step. The sample of the solution is subject to HPLC analysis; purity of this sample is 97.91%.

B. Solifenacin (R)-3-Quinuclidinol (12.15 g, 95.55 mmol) and 60% NaH (4.20 g, 105.0 mmol) are suspended in dry THF (90 mL), the resulting solution is refluxed for 45 min. To thick white suspension, (S)-1-phenyl-1,2,3,4-tetrahydroisoquinolinecarbonyl chloride in the solution of THF-heptan obtained in the prior step is added dropwise within 1 h at reflux. When addition is complete, stirring and heating is continued for 30 min. Reaction progress and total consumption of (S)-1-phenyl-1,2,3,4-tetrahydroisoquinolinecarbonyl chloride is monitored by TLC. The signal of forming product is observed in $CH_2Cl_2$—MeOH (9:1, v/v). After completion of the reaction, heating is stopped and the reaction mixture is cooled down to room temperature (20-24° C.). The solution is poured into water (100 mL). Layers are separated, water phase is extracted with toluene (3×50 mL), combined organic phases are washed with water (1×60 mL), dried ($Na_2SO_4$), filtered and condensed under reduced pressure to dryness. Creamy thick oil is obtained, which is subsequently used in the next step. Purity (HPLC) 96.09%.

Example 3

Solifenacin Succinate

Crude oily solifenacin (35 g) obtained in Example 1 is dissolved in isopropanol (100 mL) at room temperature (20-24° C.). In a separate flask the solution of succinic acid (11.30 g, 95.55 mmol) in isopropanol (130 mL) is prepared at reflux for 5 min. The hot succinic acid solution is slowly added to the solifenacin solution in isopropanol. The resulting mixture is left to reach room temperature. At ca. 45° C. the mixture turned to be cloudy and white crystalline solid begins to precipitate. The solution is left at room temperature for 2 h 30 min. The crystalline solid is filtered off and washed with cold isopropanol (10° C.) (3×40 mL), then it is dried under reduced pressure (0.1-0.15 mmHg, room temperature, 2 h) to dry mass. After two steps solifenacin succinate is obtained in 38.9 g, (84.8%) yield, of purity (HPLC) 99.39%. The final product (38 g) is recrystallized in isopropanol (150 mL), yielding 34.4 g (90.7%) of solifenacin succinate of purity (HPLC) 99.71%; $T_{(onset)}$≈150° C.

The invention claimed is:

1. A process for the preparation of solifenacin and/or pharmaceutically acceptable salt or salts thereof of high pharmaceutical purity, comprising, reacting (S)-1-phenyl-1,2,3,4-tetrahydroisoquinoline with triphosgene in the presence of a tertiary aromatic amine, in an aromatic hydrocarbon to form a reaction mixture, evaporating said reaction mixture, treating the evaporated reaction mixture with a non-polar aprotic solvent at reflux, crystallizing the treated evaporated reaction mixture at 5-15° C., isolating (S)-1-phenyl-1,2,3,4-tetrahydroisoquinolinecarbonyl chloride as crystalline solid of at least 98% purity, dissolving said crystalline solid in a polar aprotic solvent, and adding said crystalline solid in polar aprotic solvent to a suspension generated in situ of (R)-3-quinuclidinoloxy anion in the same polar aprotic solvent to acylate the (R)-3-quinuclidinoloxy anion and form solifenacin base.

2. The process according to claim 1, wherein the acylation reaction is carried out in a polar aprotic solvent, optionally in a mixture with a non-polar solvent.

3. The process according to claim 1 wherein the polar aprotic solvent comprises tetrahydrofuran, dioxane, dimethylsulfoxide, dimethylacetamide, dimethylformamide, N-methylpyrrolidon or combinations thereof.

4. The process according to claim 1, wherein the non-polar aprotic solvent comprises pentane, heptane, hexane, cyclohexane, methylcyclohexane or combinations thereof.

5. The process according to claim 1, wherein the polar aprotic solvent is tetrahydrofuran and the non-polar aprotic solvent is heptane.

6. The process according to claim 1, wherein a solution of (S)-1-phenyl-1,2,3,4-tetrahydroisoquinolinecarbonyl chloride is added to the reaction mixture at room temperature to reflux and the reaction mixture is maintained at reflux.

7. The process according to claim 1, further comprising converting the solifenacin base into solifenacin succinate without isolating solifenacin base from the reaction mixture.

8. The process according to claim 1, wherein, the (S)-1-phenyl-1,2,3,4-tetrahydroisoquinolinecarbonyl chloride is isolated in crystalline form, characterized by the interplanar spacings d (Å), diffraction angles $2\theta$ (°), and relative intensities, in attitude to the most intensive diffraction peak, $I/I_o$ (%):

| d [Å] | $2\theta$ [°] | $I/I_o$ [%] |
|---|---|---|
| 12.203 | 7.24 | 2 |
| 7.317 | 12.09 | 20 |
| 7.090 | 12.47 | 65 |
| 6.362 | 13.91 | 23 |
| 6.128 | 14.44 | 10 |
| 5.219 | 16.98 | 49 |
| 4.536 | 19.55 | 100 |
| 4.374 | 20.29 | 34 |
| 4.228 | 20.99 | 21 |
| 4.090 | 21.71 | 44 |
| 3.776 | 23.54 | 69 |
| 3.672 | 24.21 | 62 |
| 3.586 | 24.81 | 43 |
| 3.301 | 26.99 | 53 |
| 3.066 | 29.10 | 16. |

9. The process according to claim 1, wherein the tertiary aromatic amine is pyridine.

10. The process according to claim 1, wherein the (S)-1-phenyl-1,2,3,4-tetrahydroisoquinolinecarbonyl chloride is isolated as crystalline solid of at least 99% purity.

* * * * *